United States Patent [19]

Barr et al.

[11] Patent Number: 5,096,825
[45] Date of Patent: Mar. 17, 1992

[54] GENE FOR HUMAN EPIDERMAL GROWTH FACTOR AND SYNTHESIS AND EXPRESSION THEREOF

[75] Inventors: Philip J. Barr, San Francisco; James P. Merryweather; Guy T. Mullenbach, both of Berkeley; Mickey S. Urdea; Pablo Valenzuela, both of San Francisco, all of Calif.

[73] Assignee: Chiron Corporation, Emeryville, Calif.

[21] Appl. No.: 4,212

[22] Filed: Jan. 5, 1987

Related U.S. Application Data

[63] Continuation of Ser. No. 457,412, Jan. 12, 1983, abandoned.

[51] Int. Cl.$^5$ .................. C12N 15/18; C12N 15/70; C12N 15/63; C12N 1/16; C12N 1/18
[52] U.S. Cl. .................. 435/255; 435/69.4; 435/172.3; 435/252.33; 435/256; 435/320.1; 536/27; 935/13; 935/28; 935/69; 935/73
[58] Field of Search ............ 435/91, 68, 172.3, 320, 435/253, 255, 69.1, 69.4, 252.33, 256, 320.1; 935/13, 28, 69, 73; 536/27

[56] References Cited

U.S. PATENT DOCUMENTS

| | | | |
|---|---|---|---|
| 4,366,246 | 12/1982 | Riggs | 536/27 X |
| 4,387,162 | 6/1983 | Aigle et al. | 435/255 X |
| 4,719,180 | 1/1988 | Eaton et al. | 435/172.3 X |

FOREIGN PATENT DOCUMENTS

| | | | |
|---|---|---|---|
| 0046039 | 2/1982 | European Pat. Off. | 435/172.3 |
| 2068969 | 8/1981 | United Kingdom | 435/172 |

OTHER PUBLICATIONS

Hitzeman, R. et al, *Nature*, vol. 293, pp. 717–722, 1981.
Bennetzen, J. et al., *J. Biol. Chem.*, vol. 257, pp. 3018, 3026–3031, 1982.
Grantham, R. et al, *Nuc Acids Res*, vol. 8, pp. 1893–1912, 1980.
Holland, J. et al, *J. Biol. Chem.*, vol. 255, pp. 2596–2605, 1980.
Urdea, M. et al, *Proc. Natl. Acad. Sci*, vol. 80, pp. 7461–7465, Dec. 1983.
Itakura, K. et al., *Science*, vol. 209, Sep. 19, 1980, pp. 1401–1405.
Rothstein, R. et al., *Methods In Enzymology*, vol. 68, pp. 98–109, 1979.
Sentenac et al, in *The Molecular Biology of the Yeast Saccharomyces, Metabolism and Expression*, pp. 589–592, 1982, Cold Spring Harbor Laboratory.
Gregory, et al., *Int. J. Peptide Protein Research*, 9, pp. 107–118 (1977).
Khorana, H. G., *Science*, vol. 203, Feb. 16, 1979, pp. 614–625.
Edge, M. et al., *Nature* 292, 756 (1981).
Carpenter, G. et al., *Ann. Rev. Biochem.* 48, 193 (1979).
Gospodarowicz, D. *Ann. Rev. Physiol.* 43:252–63 (1981).
Letsinger et al., *J.A.C.S.* 98:12, 3655 (1976).
Crea et al., *Nucl. Acids Res.* 8, 2331 (1980).
Matteuci et al., *Tet. Lett.* 21, 719 (1980).
Beaucage et al., *Tet. Lett.* 22, 1859 (1981).
Hollenberg, M. D. et al., *Molecular Pharmacology* 17, 314 (1980).
Beggs, J., *Nature* 275, 104 (1978).
Faye G. et al., *Proc. Nat. Acad. Sci.* 78, 2258 (1981).
Schaller et al., *J.A.C.S.* 85, 3821 (1963).
Matteuci et al., *J.A.C.S.* 103, 3185 (1981).
Soberon et al., *Gene* 9, 287 (1980).
Carpenter et al., *J. Biol. Chem.* 250, 4297 (1975).

*Primary Examiner*—James Martinell
*Attorney, Agent, or Firm*—Irell & Manella

[57] ABSTRACT

A DNA having a base sequence coding for human epidermal growth factor has been synthesized in blocks, and cloned. Novel recombinant DNA transfer vectors containing said cloned DNA have been constructed. The codon usage of the sequence reflects the codon bias of yeast. The DNA sequence is useful for the large scale synthesis of human epidermal growth factor in yeast cells or microorganisms transformed by said recombinant DNA transfer vectors.

25 Claims, 4 Drawing Sheets

EcoRI Linker-1

5' GGGAATTCATG|AACTCC — TT|GAGATGATAAGAATTCC - 3'
3' CCCTTAAGTACTTGA|GG — AACTCT|ACTATTCTTAAGG - 5'

EcoRI Linker-2

EcoRI Linker-3

EcoRI Linker-4

FIG._1

HgaI Linker-1

5' AATTCGACGCTTATG|AACTCC — TT|GAGATGAATGCGTCG - 3'
3' GCTGCGAATACTTGA|GG — AACTCT|ACTTACGCAGCTTAA - 5'

HgaI Linker-2

HgaI Linker-3

HgaI Linker-4

FIG._2

GENE FOR HUMAN EPIDERMAL GROWTH FACTOR AND SYNTHESIS AND EXPRESSION THEREOF

This application is a continuation of application Ser. No. 457,412, filed Jan. 12, 1983, now abandoned.

BACKGROUND OF THE INVENTION

The synthesis of DNA by chemical methods has led to the production of a variety of synthetic genes, e.g. human leukocyte interferon gene [Edge, M. D. et al.; Nature 292, 756 (1981)]. If synthetic genes are recombined with expression vectors and transferred into the appropriate microorganism or eucaryotic cell, a genotypically and phenotypically mutant organism can be produced that can correctly transcribe and translate the artifical gene.

Applicants have synthesized and cloned a sequence coding for human epidermal growth factor (hereinafter hEGF). Applicants have employed stepwise solid-phase synthesis of oligonucleotides of single strands, followed by annealing and ligation. The codon usage in the sequence is designed for maximal expression in yeast. This invention also provides inter alia processes for cloning and amplification of the sequence coding for hEGF, methods for purifying it, and methods for constructing DNA expression vectors carrying hEGF.

Epidermal Growth Factor (EGF) has a broad spectrum of biochemical and physiological effects on cells, including, e.g., accelerated proliferation or differentiation, potentiation of limited forms of carcinogenesis, stimulation of transport, activation of glycolysis, stimulation of macromolecular synthesis, and other activities unrelated to mitogenesis, such as inhibition of gastric secretion. A useful discussion of these functions as well as review of the structure and amino acid sequence of EGF may be found in Carpenter, G. et al. Ann. Rev. Biochem., 48, 193 (1979). See also Gospodarowicz, D. Ann. Rev. Physiol. 43, 251 (1981).

Of the epidermal growth factors that have been purified to date, mouse epidermal growth factor is the best characterized as to its physical, chemical and biological properties. Mouse EGF is an acidic protein of about 53 amino acids with three disulfide bonds. In interacting with the cell, it is probable that EGF binds to a cell receptor, yielding a complex which is internalized, then degraded by lysosomes. One intriguing property is its capacity to stimulate intracellular phosphorylation of tyrosine residues, a known activity of src proteins.

Processes and methods for synthesizing DNA sequences coding for urogastrone, a polypeptide related to EGF, were published in EPO application 46,039, filed on or about July 31, 1981, by applicant G. D. Searle and Co. The Searle sequence and its corresponding protein are substantially different from the present invention for the following reasons. The DNA sequence of the Searle reference codes for a procaryote prepeptide of about an additional 14 amino acids on the amino terminus of urogastrone, an added sequence required for adequate and effective secretion in a procaryotic host. One embodiment of the present invention dispenses with a prepeptide sequence and employs a eucaryote host for propagation and expression of EGF.

Other differences between the Searle application and the present application are, secondly, that the commercial use of procaryotic cells as hosts for synthesizing human proteins requires scrupulous and expensive purification procedures to avoid the effects of pyrogens and other endotoxins. The yeast cells used in one embodiment of the present invention provide extracts entirely or substantially free of pyrogenic material, hence contaminants do not provide a hazard to the public. Yeast also provides good fermentation volume.

Thirdly, the DNA sequence of the present invention has the codon bias of yeast cells, allowing for highly efficient expression of the DNA sequence in an appropriate host cell. In addition, applicants have demonstrated expression of EGF whereas those of the Searle application have not.

Finally, the present applicants provide modifications in the techniques of solid-phase DNA synthesis that allow the synthesis of much larger blocks of single-stranded oligodeoxyribonucleotides than has previously been practical. These larger blocks reduce the number of annealing and ligation steps, a result that substantially increases the yield of final product.

The protein hEGF is useful for modulating the growth and culture of mammalian cells, particularly human cells, on a commercial scale. Potential uses include clinical treatment of wounds and ulcers.

BRIEF DESCRIPTION OF THE INVENTION

This invention relates to the synthesis of the gene coding for human epidermal growth factor by the synthesis of single-stranded blocks of DNA, followed by annealing and ligation. The sequence selected was based on yeast codon bias. Appropriate linkers are attached to each end, followed by insertion into a cloning vehicle. The DNA sequence can be inserted into a plasmid, and then expressed in a yeast cell to provide a basis for commercial scale synthesis of hEGF. The protein hEGF can be used inter alia for the propagation of eucaryotic cells in culture, and for the clinical treatment of, e.g., ulcers and wounds.

BRIEF DESCRIPTION OF THE DRAWINGS

FIG. 1 depicts EcoRI linkers.
FIG. 2 depicts HgaI linkers.

DETAILED DESCRIPTION OF THE INVENTION

Figure 3:
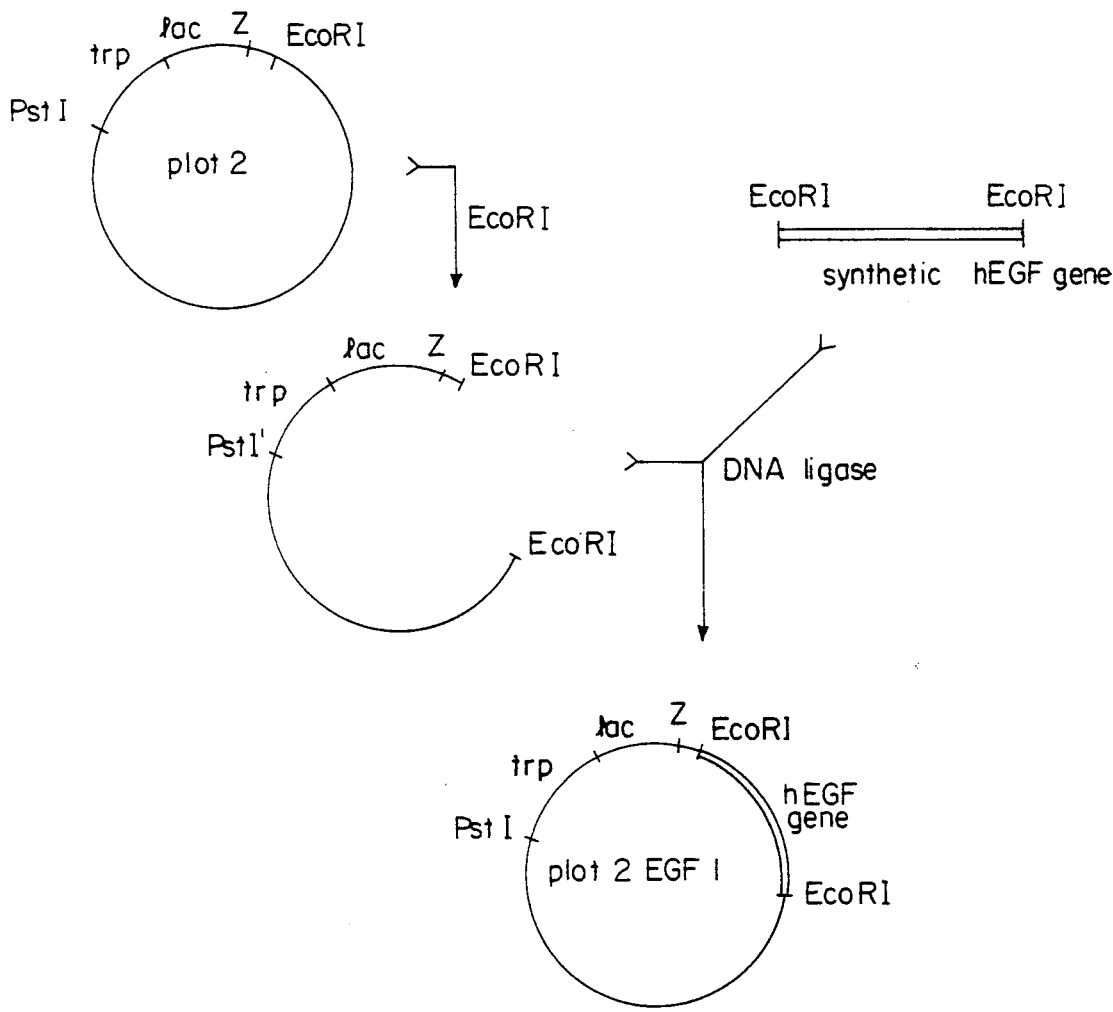
FIG. 3 illustrates the construction of a recombinant plasmid for the expression of biologically active hEGF in E. coli.

Several advances in chemical methods employed in the synthesis of DNA recently have been introduced. Letsinger and Lunsford, J.A.C.S., ,3655 (1976) showed that phosphite triester intermediates could be used to synthesize oligodeoxyribonucleotides greatly increasing the rate and ease of the coupling procedure. Several groups have employed solid-phase supported nucleosides in oligonucleotide synthesis [Crea and Horn, Nucl. Acids Res., 8, 2331 (1980); Edge et al., Nature, 292, 756 (1982)] and this has been adapted to phosphite-triester chemistry [Matteucci and Caruthers, Tet. Lett., 21, 719 (1980)]. A significant problem incurred in the phosphite method has been the chemical lability of the phosphorochloridite intermediates initially investigated. The advent of relatively stable N,N-dialkylamino phosphites has largely circumvented this problem [Beaucage and Caruthers, Tet. Lett. 22, 1859 (1981)]. Applicants have made several modifications of these procedures which increase the rate and yield of the synthetic process permitting the synthesis of larger sequences than has previously been practical.

Typically, synthetic genes are constructed from several synthetic fragments. The synthetic scheme is planned such that double-stranded segments of the gene are assembled from three or more single-stranded complementary fragments. The process involves mixing the purified rinased fragments, annealing them by heating and slow cooling, and enzymatically ligating the nicks present within the double-stranded duplex. After the partial assembly, the intermediate duplexes, by design, contain overhanging single-stranded ends that are complementary to a specific overhang on another segment. The mixing, annealing, and ligating steps are repeated with the various intermediates until the full gene is assembled. Finally, in one of a variety of methods, the gene is ligated to a specific cloning vector for characterization and expression.

The amino acid sequence of human EGF employed for the purposes of this invention is

```
                    5                    10
met—asn—ser—asp—ser—glu—cys—pro—leu—ser—his—asp—
```

```
      15                                20
gly—tyr—cys—leu—his—asp—gly—val—cys—met—tyr—ile—

25              30              35
glu—ala—leu—asp—lys—tyr—ala—cys—asn—cys—val—val—

40              45
gly—tyr—ile—gly—glu—arg—cys—gln—tyr—arg—asp—leu—

50
lys—trp—trp—glu—leu—arg
```

Note that human EGF starts at ASN, while the present applicants have synthesized an extra ATG codon for initiation.

Other EGF sequences encompassed by this invention include portions of the above sequence having physiological properties close to that of EGF. For example, an EGF without the last five amino acids on the COOH end has been found to lack mitogenic activity associated with carcinogenesis, but retain the capacity to inhibit gastric acid secretion [Hollenburg, M. D. et al. *Molecular Pharm.* 17, 314–320 (1980)]. Since the DNA sequence corresponding to a shortened hEGF sequence is shorter than that of the full-length protein, it is expected that the synthesis of the corresponding DNA sequence is easier.

The EGF gene of the present invention was designed primarily for expression in yeast systems. It is known that genes coding for highly abundant proteins in yeast exert a high degree of preference for 25 of the 61 coding triplets. The codon usage chosen for the EGF gene was based on that described for the highly expressed yeast glyceraldehyde-3-phosphate dehydrogenase (GAPDH) and alcohol dehydrogenase isozyme 1 (ADH-1) genes and is shown in Table 1.

TABLE 1

| 0/UUU/phe | 0/UCU/ser | 0/UAU/tyr | 6/UGU/cys |
|---|---|---|---|
| 0/UUC/phe | 3/UCC/ser | 5/UAC/tyr | 0/UGC/cys |
| 0/UUA/leu | 0/UCA/ser | 0/UAA/OC | 0/UGA/OP |
| 5/UUG/leu | 0/UCG/ser | 0/UAG/AM | 2/UGG/trp |
| 0/CUU/leu | 0/CCU/pro | 0/CAU/his | 0/CGU/arg |
| 0/CUC/leu | 0/CCC/pro | 2/CAC/his | 0/CGC/arg |
| 0/CUA/leu | 1/CCA/pro | 1/CAA/gln | 0/CGA/arg |
| 0/CUG/leu | 0/CCG/pro | 0/CAG/gln | 0/CGG/arg |
| 0/AUU/ile | 0/ACU/thr | 0/AAU/asn | 0/AGU/ser |
| 2/AUC/ile | 0/ACC/thr | 2/AAC/asn | 0/AGC/ser |
| 0/AUA/ile | 0/ACA/thr | 0/AAA/lys | 3/AGA/arg |
| 1/AUG/met | 0/ACG/thr | 2/AAG/lys | 0/AGG/arg |
| 3/GUU/val | 2/GCU/ala | 0/GAU/asp | 4/GGU/gly |
| 0/GUC/val | 0/GCC/ala | 5/GAC/asp | 0/GGC/gly |
| 0/GUA/val | 0/GCA/ala | 4/GAA/glu | 0/GGA/gly |
| 0/GUG/val | 0/GCG/ala | 0/GAG/glu | 0/GGG/gly |

It will be understood that the EGF gene of the present invention can also be expressed in procaryotic cells. Applicants have demonstrated expression in *E. coli* and in yeast.

The coding sequence of the EGF gene was designed as follows:

```
        HinfI
  1 AACTCCGACTCCGAATGTCCATTGTCCCACGACGGTTACTGTTTGCACGACGGTGTTTGT
    GGCTGAGGCTTACAGGTAACAGGGTGCTGCCAATGACAAACGTGCTGCCACAAACA RsaI      HindIII         RsaI                            Hph
 61 ATGTACATCGAAGCTTTGGACAAGTACGCTTGTAACTGTGTTGTTGGTTACATCGGTGAA
    TACATGTAGCTTCGAAACCTGTTCATGCGAACATTGACACAACAACCAATGTAGCCACTT
          AluI 121 AGATGTCAATACAGAGACTTGAAGTGGTGGGAATT
    TCTACAGTTATGTCTCTGAACTTCACCACCCTTAACTCT
```

A four base overhang was incorporated into the design of the gene to allow the attachment of specific linkers. The first set of linkers, designated EcoRI linkers are shown in FIG. 1. These include an ATG start codon directly adjacent to the first codon of the gene and two stop codons (TGA and TAA) directly following the last codon. The linkers also contain an EcoRI restriction site for direct cloning into the unique EcoRI site of the plasmid pBR 328, or into any other plasmid with a unique EcoRI site.

The second set of linkers, designated HgaI linkers, are shown in FIG. 2. These linkers are designed so that the gene could be cloned directly into pBR328 using EcoRI overhangs. The linkers also contain HgaI restriction sites such that after amplification of the gene in the plasmid the coding sequence can be removed directly before and after the first and last codons respectively.

As shown in FIG. 2, there is a five base overhang for use with further custom designed linkers, enabling construction of various types of expression systems. Because HgaI cleaves double-stranded DNA at five and ten base pairs away from its recognition site, and the intervening base sequence is not important to the action of the enzyme, an ATG start codon and a TGA stop codon adjacent to the coding portion of the gene are also included.

It will be understood that the linkers of FIGS. 1 and 2 are not the only kinds of linkers of use in cloning the EGF gene sequence or other related gene sequences. It is important to synthesize linkers having sequence recognition sites of restriction endonucleases, particularly for those restriction endonucleases having one cleavage site on the transfer vector, e.g., EcoRI on pBR322. The distinct advantage of the HgaI linker is that the cleavage points are at 5 and 10 bases away from the recognition site, i.e.

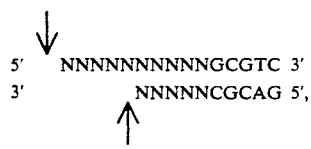

(I)

wherein N is any of A, G, C or T. Another restriction endonuclease recognition site can be built into the sequence (I) for convenient preparation and ligation of expression vectors carrying EGF sequences, e.g., yeast plasmids.

Two different types of constructions have been performed by applicants in order to express the synthetic EGF gene in yeast. In one, (pYEGF-1), a cassette with the yeast ADH promoter-EGF-gene-ADH terminator was inserted into a yeast plasmid vector which contains the entire 2 μ sequences, a DNA fragment containing the yeast leu2 gene and a fragment from pBR322 containing the origin of replication and the ampicillin resistance gene. In a second construction, (pYEGF-2), a cassette with the yeast GAPDH promoter-EGF-gene-ADH-1 terminator was inserted in the same plasmid vector as above.

Many vectors adapted for cloning in yeast include genetic markers to ensure growth of transformed yeast cells under selection pressure, for example, by including a TRP1 gene to permit the growth of a trp1 host in medium lacking tryptophan. Host cell cultures containing such vectors may contain large numbers of untransformed segregants when grown under nonselective conditions, especially when grown to high cell densities. Therefore, it is advantageous to employ expression vectors which do not require growth under selection conditions, in order to permit growth to high densities and to minimize the proportion of untransformed segregants. Vectors which contain a substantial portion of the naturally occurring two micron circle plasmid are able to replicate stably with minimal segregation of untransformed cells, even at high cell densities, when transformed into host strains previously lacking two micron circles. Such host strains are termed circle zero (cir⁰) strains. Additionally, the rate of cell growth at low cell densities may be enhanced by incorporating regulatory control over the promoter such that the expression of the EGF coding region is minimized in dilute cultures such as early to middle log phase, then turned on for maximum expression at high cell densities. Such a control strategy increases the efficiency of cell growth in the fermentation process and further reduces the frequency of segregation of untransformed cells.

In the examples that follow, many of the techniques, reactions and separation procedures are already well known in the art. All enzymes, unless otherwise stated, are available from one or more commercial sources, such as New England BioLabs, Beverly, Mass.; Collaborative Research, Waltham, Mass.; Miles Laboratories, Elkhart, Ind.; Boehringer Biochemicals Inc., Indianapolis, Ind.; and Bethesda Research Laboratory, Rockville, Md. Buffers and reaction conditions for restriction enzyme digestion were used according to recommmendations supplied by the manufacturer for each enzyme. Partial digestions with restriction enzymes were carried out using a reduced enzyme concentration which was predetermined from preliminary experiments for each enzyme batch. Standard methodology for other enzyme reactions, gel electrophoresis separations and *E. coli* transformation may be found in *Methods in Enzymology*, Vol. 68, Ray Wu, Ed., Academic Press (1979). Transformation of yeast protoplasts can be carried out essentially as described by Beggs, *Nature* 275, 104–109 (1978).

*E. coli* strains useful for transformation include X1776; K12 strain 294 (ATCC No. 31446); RR1 and HB101. Yeast strains GM-3C-2, Faye, G. et al., *Proc. Nat. Acad. Sci. USA* 78, 2258 (1981) Genotype: (Leu2 Trp1 His4 CYC1-1 CYP3-1)(ATCC No. 20659), 2150-2-3 (a, ade1 leu2 cir⁰); XV610-8C (a, ade2, ade6 leu2 lys1 trp1 can1 SF657-9C-AB102 (a, pep4, leu2 ura2 his4 cir⁰), are typically used for yeast transformations. Commercial strains of yeast can also be used for transformation, e.g. Fleischmann's yeast. Bacteria can be grown and selected according to procedures described by Miller, J. H., *Experiments in Molecular Genetics*, Cold Spring Harbor Laboratory, Cold Spring Harbor, N.Y. (1972). Yeast can be grown on the following media: YEPD containing 1% (w/v) yeast extract, 2% (w/v) peptone, and 2% (w/v) glucose; and, in the case of plating media, 3% (w/v) agar. YNB plus CAA contains 6.7 grams of yeast nitrogen base (Difco Laboratories, Minneapolis, Minn.), 10 mg of adenine, 10 mg of uracil, 5 g casamino acids (CAA) (Difco), 20 g glucose; and, in the case of plating media, 30 g agar per liter. Selection for tryptophan prototrophy can be made on plates containing 6.7 g yeast nitrogen base (lacking amino acids), and supplemented for all growth requirements of the strain to be transformed except tryptophan.

EXAMPLE 1

Oligonucleotide Synthesis

The oligonucleotides making up the coding sequence of the EGF gene and the two sets of linker molecules were synthesized by a modification of the method of Beaucage and Caruthers, *Tet. Lett.*, 22, 1859 (1981) and references therein. Starting materials for the synthesis were the 5'-O-dimethoxytrityl derivatives of N-benzoyl-2'-deoxyadenosine, N-benzoyl-2'-deoxycytosine N-isobutyryl-2'-deoxyguanosine and thymidine. These were synthesized as described by Schaller et al. *J.A.C.S.*, 85, 3821 (1963) except that isobutyryl chloride was used to protect 2'-deoxyguanosine instead of isobutyric anhydride. Deprotection of the 3'- and 5'-hydroxyl functionalities was carried out by adjusting the solutions to pH 13 with 2N NaOH. The progress of the reaction was followed by TLC on silica gel using methanol-chloroform (1:9) as the mobile phase. After completion of the reaction, the solutions were neutralized with the pyridinium form of Dowex 50W-X8. The resin was washed with 40% aqueous ethanol and the combined washings were evaporated under reduced pressure to a small volume. The resulting precipitate was washed and powdered with anyhydrous ether. The fully protected 2'-deoxynucleosides were converted to their N,N-dimethylaminophosphoramidites as described by Beaucage and Caruthers, supra (1981). Solid phase synthesis of oligonucleotides by sequential addition of the above monomer units proceeded as follows:

To 50mg (ca 3 micromoles) of the appropriately protected deoxynucleoside, covalently linked to a silica gel support by a 3'-succinate ester linkage, [Matteuci and Caruthers, J.A.C.S., 103, 3185 (1981)] was added a twenty fold excess of the appropriate deoxynucleoside phosphoramidite in a 0.33M solution of tetrazole in acetonitrile (0.75 ml). The slurry was shaken for 2 minutes and then washed with acetonitrile (3 ml). Unreacted 5'hydroxyl groups were acetylated using acetic anhydride (50 ml) in a 6.5% solution of N, N-dimethylaminopyridine in lutidine-THF (1:9) (0.5 ml), for 4 minutes. After washing the acetylation solution from the support with 3 ml of THF-lutidine-water (2:1:1), the intermediate phosphite was oxidized using 2 ml of a 0.2M solution of iodine in THF-lutidine-water (2:2:1) for 0.5 minutes. This solution was washed from the support using acetonitrile (3 ml) followed by dichloromethane (3 ml). The 5'-O-dimethoxytrityl group was cleaved using 5% (w/v) dichloroacetic acid in dichloromethane. This gave a free 5'-hydroxyl suitable for further sequential coupling by repetition of the above reaction sequence.

After completion of the desired length oligonucleotide, the methyl protecting groups were removed from the phosphate backbone using thiophenol-triethylamine-dioxane (1:1:2) (1 ml). The oligonucleotide was cleaved from the silica support and base protecting groups were removed using concentrated ammonium hydroxide. The 5'-O-dimethexytrityl group was removed using 80% acetic acid and the fully deprotected oligonucleotide was purified by preparative gel electrophoresis in 15 or 20% acrylamide and 7M urea.

EXAMPLE 2

Assembly Scheme of Oligodeoxynucleotides for Synthesis of DNA Coding for hEGF.

To synthesize the sequence

```
                    HinfI
1 5' AACTCCGACTCCGAATGTCCATTGTCCCACGACGGTTACTGTTTGCACGACGGTGTTTGT
       GGCTGAGGCTTACAGGTAACAGGGTGCTGCCAATGACAAACGTGCTGCCACAAACA RsaI         HindIII        RsaI                                Hph
61 ATGTACATCGAAGCTTTGGACAAGTACGCTTGTAACTGTGTTGTTGGTTACATCGGTGAA
    TACATGTAGCTTCGAAACCTGTTCATGCGAACATTGACACAACAACCAATGTAGCCACTT AluI 121 AGATGTCAATACAGAGACTTGAAGTGGTGGGAATT
     TCTACAGTTATGTCTCTGAACTTCACCACCCTTAACTCT,
``` a total of 12 pieces varying in length from 12 to 33 nucleotides were made according to Example 1. The position of each piece, the individual sequence and size are as follows:

| E1 | E2 | E3 | E4 | E5 | E6 |
| E7 | E8 | E9 | E10 | E11 | E12 |

E1 AACTCCGACTCCGAATGTCCATT - 23 mer
E2 GTCCCACGACGGTTACTGTTTGCACGACGGTGT - 33 mer
E3 TTGTATGTACATCGAAGCTTTGGACAAGTA - 30 mer
E4 CGCTTGTAACTGTGTTGTTGGTTACATCG - 29 mer
E5 GTGAAAGATGTCAATACAGAGAC - 23 mer
E6 TTGAAGTGGTGGGAATT - 17 mer
E7 ATTCGGAGTCGG - 12 mer
E8 GCAAACAGTAACCGTCGTGGGACAATGGAC - 30 mer
E9 CCAAAGCTTCGATGTACATACAAACACCGTCGT - 33 mer
E10 AACACAGTTACAAGCGTACTTGT - 23 mer
E11 TTGACATCTTTCACCGATGTAACCAAC - 27 mer
E12 TCTCAATTCCCACCACTTCAAGTCTCTGTA - 30 mer The assembly scheme for these DNA segments of the E series, E1-E12, is described in example 3.

EXAMPLE 3

Ligation of DNA Pieces

An aliquot of 10 μg of E1 was phosphorylated using 6 units of T4 induced polynucleotide kinase in 30 μl of a solution containing 50 mM Tris-HCl (pH 7.8), 10 mM MgCl$_2$, 3 mM ATP and 10 mM DTT for 1 hour at 37°. Kinase was inactivated by heating at 90° for 5 minutes.

This kinasing procedure was repeated for each DNA segment of the E series (see Example 2) and for EcoRI linkers 2 and 3, and for HgaI linkers 2 and 3. EcoRI linkers 1 and 4 and HgaI linkers 1 and 4 were not kinased. Segments of the E series were then mixed in the presence of EcoRI linkers in three separate reaction mixtures as follows:

| REACTION MIXTURE | SEGMENT | LIGATION PRODUCT |
|---|---|---|
| 1 | E1, E2 and EcoRI linker 1 | A |
|   | E7, E8, E9 and EcoRI linker 2 | B |
| 2 | E3, E4 | C |
|   | E10 | D |
| 3 | E5, E6 and EcoRI linker 3 | E |
|   | E11, E12 and EcoRI linker 4 | F |

The DNA of each reaction mixture was ethanol precipitated and resuspended in a solution (20 μl) containing 50 mM Tris-HCl (pH 7.8), 10 mM MgCl$_2$ and 1 mg/ml spermidine. The solutions were heated to 85° and slow cooled to 20° at 0.1° C. per minute. The solution was then made 10 mM in DTT, 3 mM in ATP, and T4 DNA ligase (6 units) was added. After 2h at 20° C. the solutions were evaporated to dryness and single-stranded ligation products (A-F) were separately isolated by gel electrophoresis in 15% polyacrylamide and 7M urea. For the final gene ligation, fragments A-F (2 pmoles of each) were mixed in 30 μl of the above ligation buffer and annealed and ligated as described above. After 2h at 20° the DNA was ethanol precipitated, resuspended in 20 μl of a buffer containing 0.1 M Tris-HCl pH 7.2, 50 mM MgCl$_2$, 2 mM 2-mercaptoethanol and 50 mM NaCl. EcoRI (20 units) was added and after 2h the ligation product was purified on a 7% polyacrylamide gel. Bands were visualized by ethidium bromide staining and a band corresponding to 170 base-pairs was electroeluted for cloning into pBR328 [Soberon et al., Gene 9, 287 (1980)].

EXAMPLE 4

Cloning and Amplification in pBR328

The electroeluted DNA fragment was ligated to pBR328 (previously linearized with EcoRI and treated with calf intestine alkaline phosphatase) and used to transform competent E. coli cells. Recombinants were analyzed by their resistance to ampicillin and sensitivity to chloramphenicol. Plasmids from positive colonies were analyzed and found to contain a fragment of the expected size (170 base pairs) after EcoRI digestion.

The 170-bp fragment from one plasmid, pBEGF-1, was preparatively isolated and sequenced. The sequence obtained was identical to the sequence designed for the synthetic hEGF gene.

EXAMPLE 5

Fibroblast receptor competition binding assay for EGF

The assay of EGF is based on the ability of both mouse and human EGF to compete with $^{125}$I-labeled mouse EGF for binding sites on human foreskin fibroblasts. Standard curves can be obtained by measuring the effects of increasing quantities of EGF on the binding of a standard amount of $^{125}$I-labeled mouse EGF. Under these conditions 2 to 20 ng of EGF are readily measurable. Details on the binding of $^{125}$I-labeled epidermal growth factor to human fibroblasts have been described by Carpenter et al., J. Biol. Chem. 250, 4297 (1975).

EXAMPLE 6

Expression of hEGF in E. coli

Preliminary expression of biologically active hEGF from the synthetic gene was obtained in E. coli as a fused protein with the first 9 N-terminal amino acids of beta-galactosidase (lac Z gene). The expression vector plot 2 was linearized with the restriction enzyme EcoRI, ligated to the EcoRI synthetic fragment containing the hEGF gene (plot 2 EGF-1) and used to transform E. coli D1210 (FIG. 3). Colonies were analyzed for plasmid structure and those containing the EGF gene in the correct orientation with respect to the trp-lac operator-promoter region were selected for further analysis (plot 2 EGF-1). Twenty ml cultures of cells were grown to an optical density at 650 nm of 0.5, induced with 2 mM final IPTG (isopropyl thiogalactoside) and grown again for 2 more hours. Cell lysates were prepared by lysozome digestion, treatment with Triton X-100 and DNAse I. After centrifugation clear cell lysates containing approximately 10 mg/ml of protein were analyzed for hEGF.

The results are summarized in Table 2. In contrast to cells that were not induced, cells treated with IPTG produced easily detectable EGF activity in the receptor competition binding assay of Example 7. The amount synthesized was calculated to be 32 ng of hEGF per mg of protein or about 1600 molecules of hEGF per cell.

These results indicate that biologically active hEGF was synthesized under trp-lac control from the synthetic gene.

TABLE 2

| Expression of Biologically Active EGF in E. coli | | | |
|---|---|---|---|
| E. coli Extract | EGF/mg Protein, ng | EGF % Total Protein | Molecules/ Cell |
| Uninduced | 0 | 0.0000 | 0 |
| Induced | 32 | 0.0032 | 1600 |

EXAMPLE 7

Construction of pYEGF-1

The synthetic EGF gene was isolated by digesting to completion 100 μg of p328EGF-1 (a plasmid containing the synthetic EGF gene cloned in the EcoRI site of pBR328) with the restriction enzyme EcoRI. Approximately 2 μg of the expected 190 base pair EcoRI fragment was isolated by preparative gel electrophoresis (see FIG. 4).

The yeast vector plasmid was a derivative of plasmid pCl/1 (this is a derivative of plasmid pJDB219, J. D. Beggs, Nature, 275, 104 (1978), in which the region corresponding to bacterial plasmid pMB9 in pJDB219 has been replaced by a region of pBR322 in pCl/1).

Figure 4:
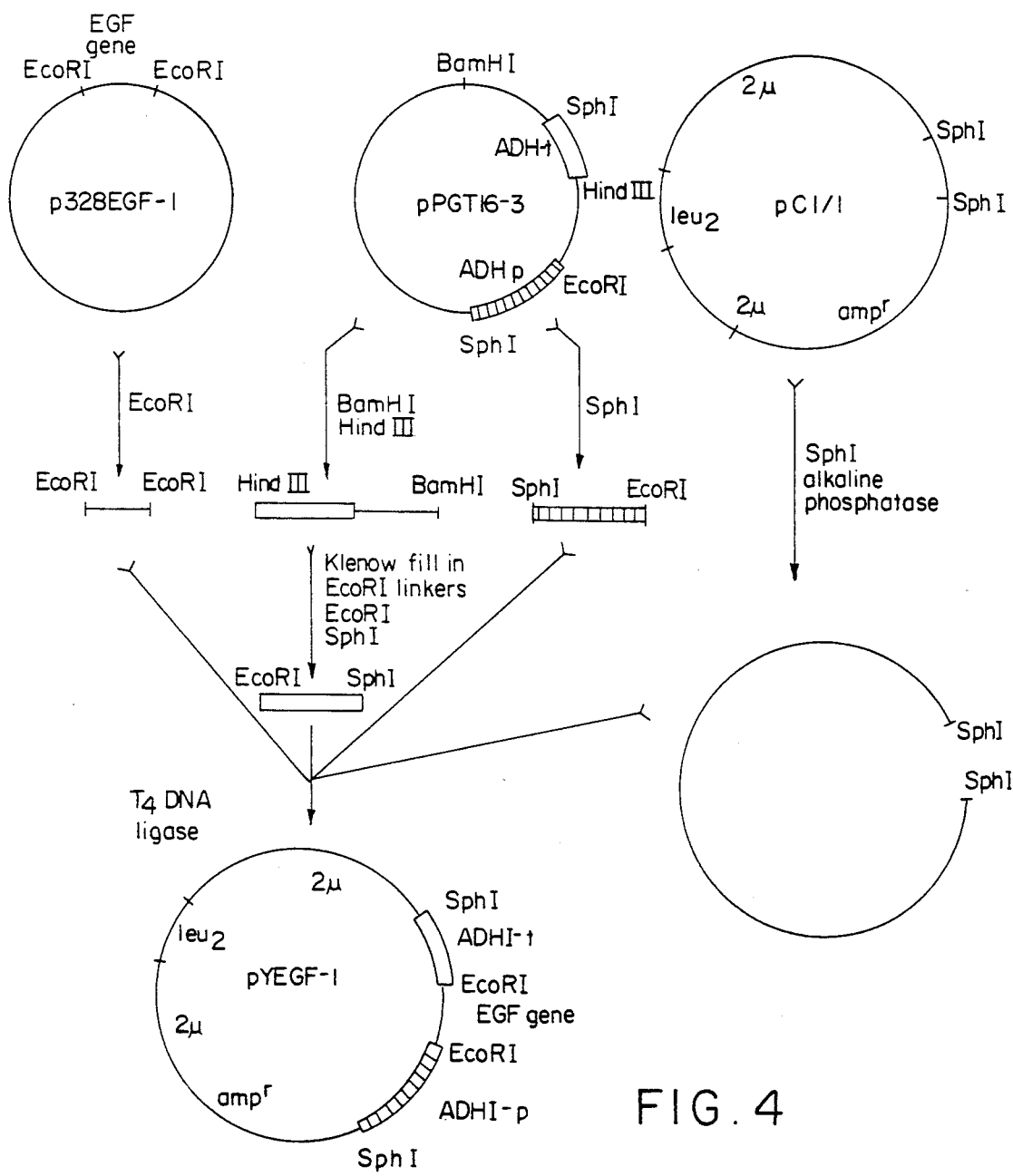
FIG. 4 illustrates the construction of pYEGF-1.

The yeast ADH-1 promoter and terminator regions were isolated from plasmid pPGT16-3 (this plasmid was prepared from the data of J. L. Bennentzen and B. D. Hall, J. Biol. Chem. 257, 3018 (1982)) as indicated in FIG. 4. One hundred μg of pPGT16-3 was digested to completion in the restriction enzymes BamHI and HindIII. A fragment of approximately 570 base pairs was preparatively isolated by gel electrophoresis. Approximately 5 μg of this fragment was filled in with Klenow fragment, then ligated to EcoRI linkers and finally digested to completion with the restriction endonucleases SphI and EcoRI. Approximately 2 μg of a 380 base-pair EcoRI-SphI fragment containing the yeast ADH-1 terminator region was isolated by preparative gel electrophoresis. One hundred μg of pPGT16-3 was digested to completion with the restriction enzymes SphI and EcoRI. An EcoRI-SphI fragment of approximately 380 base pairs containing the yeast ADH-1 promoter region was isolated by gel electrophoresis. 50 μg of pCl/1 was digested to completion with the restriction enzyme SphI and treated with alkaline phosphatase. The plasmid vector for the expression of EGF in yeast was assembled as follows: 25 ng of the synthetic EGF gene EcoRI fragment, 60 ng of the SphI-EcoRI yeast ADH-1 promoter fragment and 55 ng of the EcoRI-SphI yeast ADH-1 terminator fragment were ligated together in the presence of T$_4$ DNA ligase, digested with the restriction enzyme SphI and ligated to 50 ng of SphI-digested pCl/1. The resulting mixture was used to transform E. coli HB101 cells. Transformants were selected by ampicillin resistance and their plasmids were analyzed by mapping with restriction endonucleases. DNA from a selected clone (pYEGF-1), in which the promoter, gene and termination regions were in the correct relative orientation, was prepared and used to transform yeast GM 3C2 (leu2, trp1, his4, cyc1-1, cyc3-1) cells. Transformants were selected by their leu+ phenotype.

EXAMPLE 8

Construction of pYEGF-2

Figure 5:
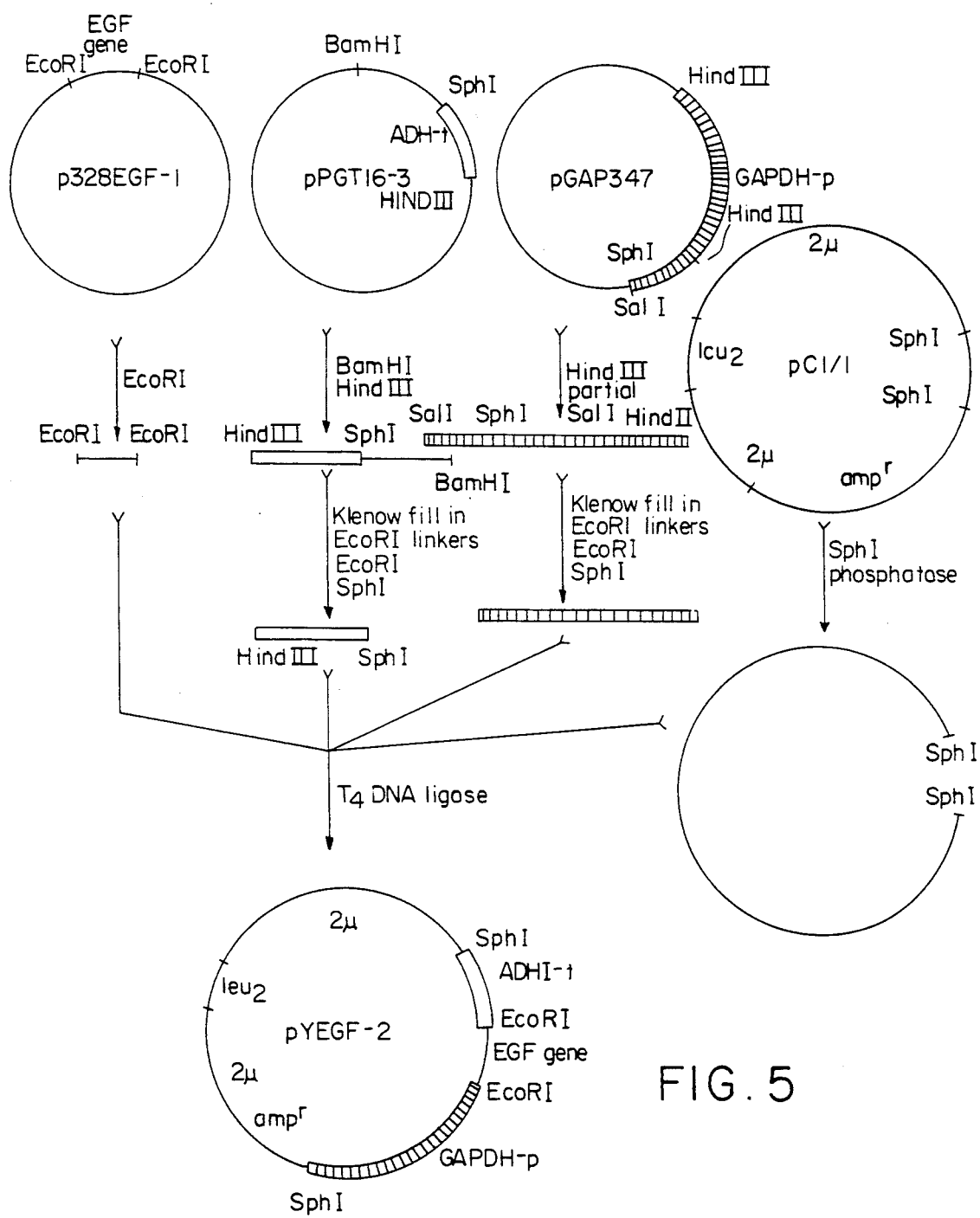
FIG. 5 illustrates the construction of pYEGF-2.

This plasmid is similar to pYEGF-1 except for having a yeast GAPDH promoter region instead of the yeast ADH-1 promoter region. The yeast GAPDH promoter fragment was isolated from pGAP347, a plasmid which contains the GAPDH promoter region cloned as a 1200 base-pair HindIII fragment in pBR322 (FIG. 5). One hundred μg of pGAP347 was digested to completion with SalI and partially with HindIII. The resulting Hind-SalI fragment of approximately 1800 base pairs was isolated by preparative gel electrophoresis. Three μg of this fragment was filled in with Klenow fragment, then ligated to an excess of EcoRI linkers in the presence of T4 DNA ligase and finally digested to completion with the restriction enzymes SphI and EcoRI. A SphI-EcoRI fragment of approximately 1700 base pairs was isolated by preparative gel electrophoresis.

The pYEGF plasmid was assembled as follows: 25 ng of the synthetic EGF gene EcoRI fragment (obtained from p328EGF-1 as described for pYEGF-1 of Example 7), 200 ng of the SphI yeast GAPDH promoter fragment and 55 ng of the EcoRI-SphI yeast ADH-1 terminator fragment (obtained from pPGT16-3 as described for pYEGF-1 of Example 7), were ligated together in the presence of T4 DNA ligase, digested with the restriction enzyme SphI and ligated to 50 ng of SphI-digested pCl/1. The resulting mixture was used to transform E. coli HB101 cells. Transformants were selected by amplicillin resistance and their plasmids were analyzed by mapping with restriction endonucleases. DNA from a selected clone (pYEGF-2) in which the promoter, gene and terminator were in the correct relative orientation, was prepared and used to transform yeast GM3C2 cells. Transformants were selected by their leu+ phenotype.

EXAMPLE 9

Expression of Human EGF in Yeast

Fifty ml cultures of yeast strain GM3C2 transformed with either plasmid pYEGF-1 or pYEGF-2 were grown to optical density at 600 of 2 to 3. The cells were harvested by centrifugation and washed with lysis buffer, 10 mM $Na_2HPO_4$ (pH 7.5), 0.1% Triton X-100. For breakage, one volume of packed cells were vortexed with one volume of lysis buffer and 1 volume of glass beads for 5 minutes at 4° C. After centrifugation clear lysates containing 15 to 20 mg/ml of protein are analyzed by the EGF receptor binding competition assay. The results are shown in Table 3.

TABLE 3

| Expression of biologically active human EGF in yeast | | | |
|---|---|---|---|
| Yeast cells extract | ng EGF/mg protein | EGF % of total protein | Molecules/cell |
| GM3C2 | 0 | 0 | 0 |
| GM3C2 transformed with pYEGF-1 | 5 | 0.0005 | 2,500 |
| GM3C2 transformed with pYEGF-2 | 40 | 0.004 | 20,000 |

The plasmids plot 2-EGF-1, pYEGF-1, pYEGF-2, and yeast cells GM3C2 containing pYEGF-1 and GM3C2 containing pYEGF-2 have been deposited with the American Type Culture Collection located at 12301 Parklawn Drive, Rockville, Md., on or before the filing of the present application, and have received ATCC designation numbers 40060, 40058, 40059, and 20659-20660, respectively. Escherichia coli D 1210 containing plot 2-EGF-1 has also been deposited with the ATCC where it has received ATCC designation number 39267.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. DNA of the sequence for human epidermal growth factor comprising

5' ATGAACTCCGACTCCGAATGTCCATTGTCCC
TACTTGAGGCTGAGGCTTACAGGTAACAGGG

ACGACGGTTACTGTTTGCACGACGGTGTTTGTA
TGCTGCCAATGACAAACGTGCTGCCACAAACAT

TGTACATCGAAGCTTTGGACAAGTACGCTTGT
ACATGTAGCTTCGAAACCTGTTCATGCGAACA

AACTGTGTTGTTGGTTACATCGGTGAAAGATGTC
TTGACACAACAACCAATGTAGCCACTTTCTACAG

AATACAGAGACTTGAAGTGGTGGGAATTGAGATGA
TTATGTCTCTGAACTTCACCACCCTTAACTCTACT, encoding for physiologically active human epidermal growth factor, having a promoter-proximal end and a promoter-distal end, wherein the 5' terminal ATG designates the coding strand and the promoter-proximal end of the sequence.

2. DNA of the sequence for human epidermal growth factor comprising the sequence of claim 1 ligated at each end to double-stranded linkers containing recognition sites for restriction endonucleases.

3. DNA of the sequence for human epidermal growth factor according to claim 2 wherein both of said double-stranded linkers contain a recognition site for EcoRI restriction endonuclease.

4. DNA of the sequence for human epidermal growth factor according to claim 2 wherein both of said double-stranded linkers contain a recognition site for HgaI restriction endonuclease.

5. A DNA sequence of claim 1 further comprising DNA of a transfer vector.

6. A DNA expression vector which comprises a yeast promoter ligated at the promoter-proximal end of the sequence of claim 1, said sequence being under transcriptional control of said yeast promoter.

7. A DNA expression vector which comprises a yeast promoter ligated at the promoter-proximal end of the sequence of claim 1, said sequence being under transcriptional control of said yeast promoter; and a terminator region ligated at the promoter-distal end of said sequence.

8. A DNA expression vector according to claim 7 wherein said terminator region is from yeast.

9. A DNA expression vector of claim 6 wherein said yeast promoter comprises the GAPDH yeast promoter.

10. A DNA expression vector of claim 6 wherein said yeast promoter comprises the ADH-1 promoter.

11. A DNA expression vector of claim 7 wherein said yeast promoter comprises the GAPDH yeast promoter and said terminator region comprises the ADH-1 terminator.

12. A DNA expression vector of claim 7 wherein said yeast promoter comprises the ADH-1 yeast promoter and said terminator region comprises the ADH-1 terminator.

13. A yeast transformed by the DNA expression vector of claim 6.

14. A yeast transformed by the DNA expression vector of claim 7.

15. A yeast transformed by the DNA expression vector of claim 8

16. A yeast transformed by the DNA expression vector of claim 9.

17. A yeast transformed by the DNA expression vector of claim 10.

18. A yeast transformed by the DNA expression vector of claim 11.

19. A yeast transformed by the DNA expression vector of claim 12.

20. The DNA expression vector plot 2 EGF-1.

21. The DNA expression vector pYEGF-1.

22. The DNA expression vector pYEGF-2.

23. The yeast GM3C2 transformed by pYEGF-1.

24. The yeast GM3C2 transformed by pYEGF-2.

25. *E. coli* D1210 transformed by plot 2 EGF-1.

* * * * *